United States Patent
Moore et al.

(10) Patent No.: US 10,094,754 B2
(45) Date of Patent: Oct. 9, 2018

(54) PRESSURE INDICATOR FOR HYDRAULIC HAMMER

(71) Applicant: Caterpillar Inc., Peoria, IL (US)

(72) Inventors: Cody T. Moore, Waco, TX (US); Lauritz P. Pillers, McGregor, TX (US)

(73) Assignee: Caterpillar Inc., Deerfield, IL (US)

( * ) Notice: Subject to any disclaimer, the term of this patent is extended or adjusted under 35 U.S.C. 154(b) by 396 days.

(21) Appl. No.: 14/966,772

(22) Filed: Dec. 11, 2015

(65) Prior Publication Data
US 2017/0167962 A1    Jun. 15, 2017

(51) Int. Cl.
| | | |
|---|---|---|
| *E21B 15/04* | (2006.01) | |
| *G01N 7/00* | (2006.01) | |
| *B25D 9/00* | (2006.01) | |
| *B25D 9/14* | (2006.01) | |

(52) U.S. Cl.
CPC .......... *G01N 7/00* (2013.01); *B25D 9/00* (2013.01); *B25D 9/145* (2013.01); *B25D 2209/002* (2013.01); *B25D 2250/155* (2013.01); *B25D 2250/161* (2013.01)

(58) Field of Classification Search
CPC .......... E21B 21/08; E21B 2034/007; E21B 47/1025; B25D 9/145; B25D 2209/002; B25D 2250/125; B25D 2250/155; B25D 2250/161; B25D 9/00; G01N 7/00
USPC ............................................ 173/2, 184, 200
See application file for complete search history.

(56) References Cited

U.S. PATENT DOCUMENTS

| | | | |
|---|---|---|---|
| 3,662,333 A | | 5/1972 | Howard et al. |
| 3,677,334 A | | 7/1972 | Bathla et al. |
| 3,681,918 A | | 8/1972 | Chanin |
| 3,862,646 A | | 1/1975 | Tarsha |
| 3,967,771 A | * | 7/1976 | Smith ............... B25C 1/08 227/10 |
| 4,207,563 A | | 6/1980 | Soupal |
| 4,461,937 A | | 7/1984 | Boni |
| 4,534,500 A | * | 8/1985 | Jochum ............... B25C 1/008 173/13 |
| 4,601,349 A | * | 7/1986 | Arentsen ............... E02D 7/10 173/200 |
| 5,458,608 A | * | 10/1995 | Wortrich ........... A61B 17/00234 227/110 |
| 7,356,990 B2 | | 4/2008 | Burdick et al. |
| 7,677,334 B2 | * | 3/2010 | Blount ............... E21B 4/18 175/107 |

(Continued)

*Primary Examiner* — Robert Long

(57) ABSTRACT

A pressure indicator for a hydraulic hammer is provided. The pressure indicator includes a sleeve member configured to couple to an opening defined in a wall housing of an accumulator of the hydraulic hammer. The pressure indicator further includes a plunger slidably disposed within the sleeve member and movable between a first position and a second position with respect to the sleeve member. The plunger includes a first end disposed outside the wall housing of the accumulator. The plunger further includes a flange coupled to a second end. The pressure indicator further includes an elastic member inserted over the plunger and disposed between the wall housing of the accumulator and the flange. A position of the first end of the plunger with reference to an outer end of the sleeve member provides a visual indication of the pressure of the gas within the accumulator.

16 Claims, 8 Drawing Sheets

(56) References Cited

U.S. PATENT DOCUMENTS

2009/0152006 A1\* 6/2009 Leduc .................... E21B 21/08
  175/48
2013/0082083 A1\* 4/2013 Largo ..................... B25C 1/041
  227/8
2015/0000756 A1 1/2015 Chen et al.
2015/0075833 A1\* 3/2015 Dotan .................... B23Q 5/06
  173/218

\* cited by examiner

PRESSURE INDICATOR FOR HYDRAULIC HAMMER

TECHNICAL FIELD

The present disclosure relates to a hydraulic hammer, and more particularly relates to a pressure indicator for the hydraulic hammer.

BACKGROUND

Hydraulic hammers are used at work sites to break up large and hard objects before such objects can be moved away. Generally, hydraulic hammers are coupled to machines, such as excavators or other machines. A hydraulic hammer includes a piston that is moved against a volume of gas in an accumulator coupled to a power cell of the hydraulic hammer, thereby compressing the volume of gas. The compressed volume of gas further facilitates downward movement of the piston. As such, the accumulator needs to be charged by the gas at a desired pressure. Usually, the gas inside the accumulator can only be checked but not refilled. Charging the accumulators of the hydraulic hammer without knowing actual pressure of the gas may lead to higher operation cost as charging of the accumulator is expensive and complex.

U.S. Pat. No. 7,356,990 (the '990 patent) discloses an electro hydraulic actuator with built-in fail safes. Multiple accumulators are integrated into the actuator to improve reliability and redundancy. One or more accumulators can fail and the remaining accumulators provide sufficient energy to move the actuator to its fail-safe condition. The '990 patent replaces the membrane and nitrogen charged base accumulator with a spring-loaded piston accumulator. With the use of multiple accumulators built into the actuator, any accumulator can cease to function properly when required and the other accumulators will fully stroke the actuator/valve to its fail-safe condition.

SUMMARY OF THE DISCLOSURE

In one aspect of the present disclosure, a pressure indicator for a hydraulic hammer is provided. The pressure indicator includes a sleeve member configured to couple to an opening defined in a wall housing of an accumulator of the hydraulic hammer. The pressure indicator further includes a plunger slidably disposed within the sleeve member and movable between a first position and a second position with respect to the sleeve member. The plunger includes a first end disposed outside the wall housing of the accumulator. The plunger further includes a flange coupled to a second end. The second end is distal to the first end, and disposed inside the wall housing of the accumulator. The pressure indicator further includes an elastic member inserted over the plunger and disposed between the wall housing of the accumulator and the flange. The plunger is movable between the first position and the second position relative to the sleeve member against a biasing force of the elastic member based on a pressure of gas within the accumulator. A position of the first end of the plunger with reference to an outer end of the sleeve member provides a visual indication of the pressure of the gas within the accumulator.

In another aspect of the present disclosure, a hydraulic hammer is provided. The hydraulic hammer includes a housing member and a power cell disposed within the housing member. The power cell includes an accumulator for storing gas. The accumulator includes a pressure indicator configured to provide a visual indication of a pressure of the gas within the accumulator. The pressure indicator includes a sleeve member configured to couple to an opening defined in a wall housing of an accumulator of the hydraulic hammer. The pressure indicator further includes a plunger slidably disposed within the sleeve member and movable between a first position and a second position with respect to the sleeve member. The plunger includes a first end disposed outside the wall housing of the accumulator. The plunger further includes a flange coupled to a second end. The second end is distal to the first end, and disposed inside the wall housing of the accumulator. The pressure indicator further includes an elastic member inserted over the plunger and disposed between the wall housing of the accumulator and the flange. The plunger is movable between the first position and the second position relative to the sleeve member against a biasing force of the elastic member based on a pressure of gas within the accumulator. A position of the first end of the plunger with reference to an outer end of the sleeve member provides a visual indication of the pressure of the gas within the accumulator.

In yet another aspect of the present disclosure, a method for visual indication of a pressure of gas within an accumulator of a hydraulic hammer is provided. The method includes receiving a plunger within an opening defined in a wall housing of the accumulator. The plunger includes a first end disposed outside the wall housing of the accumulator and a second end having a flange disposed inside the wall housing of the accumulator. The plunger is movable between a first position and a second position with respect to a sleeve member coupled to the opening. The method further includes receiving, via the flange of the plunger, an input indicative of the pressure of the gas within the accumulator. The method further includes moving the plunger relative to the sleeve member against a biasing force caused by an elastic member. A position of the first end of the plunger with reference to the sleeve member provides the visual indication of the pressure of the gas within the accumulator.

Other features and aspects of this disclosure will be apparent from the following description and the accompanying drawings.

DETAILED DESCRIPTION

Reference will now be made in detail to specific embodiments or features, examples of which are illustrated in the accompanying drawings. Wherever possible, corresponding or similar reference numbers will be used throughout the drawings to refer to the same or corresponding parts.

Figure 1:
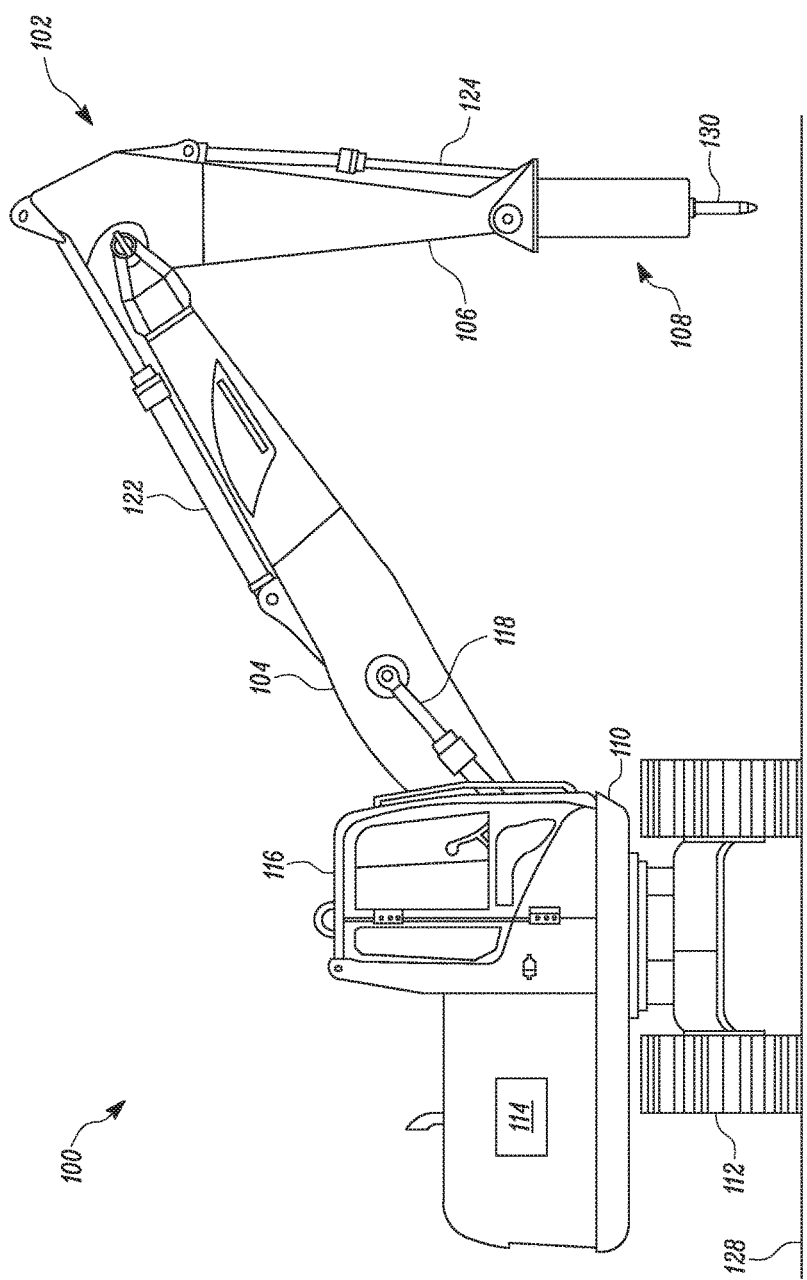
FIG. 1 is a side view of an exemplary machine including a hydraulic hammer coupled to an implement system of the machine, according to an embodiment of the present disclosure.

FIG. 1 illustrates a side view of an exemplary machine 100 having an implement system 102. The machine 100 may include, but is not limited to, an excavator, a material handler, a long reach excavator, a foundation drill, a rock drill, a piling machine, a tunneling machine, and a front shovel. In the illustrated embodiment, the machine 100 is shown as an excavator-type earthmoving or logging machine having the implement system 102. The implement system 102 includes linkages, such as a boom 104 and a stick 106. The boom 104 may be pivotally connected to a chassis 110 of the machine 100 and the stick 106 may be pivotally connected to the boom 104. The machine 100 further includes a hydraulic hammer 108 pivotally connected to the stick 106. The machine 100 may also include a drive system 112, such as tracks for propelling the machine 100, a power source 114 to power the implement system 102 and the drive system 112, and an operator cab 116 having user interface devices for controlling the implement system 102 and the drive system 112. The power source 114 of the hydraulic hammer 108 may embody an engine, such as a diesel engine, a gasoline engine, a gaseous fuel-powered engine or any other type of combustion engine known in the art. The power source 114 may alternatively embody a non-combustion source of power such as a fuel cell, a power storage device, or any other source known in the art. The power source 114 may produce mechanical or electrical power output that may be converted to hydraulic power for moving the implement system 102. The hydraulic power may be further supplied to the hydraulic hammer 108 for operation of the hydraulic hammer 108 during earth moving operation of the machine 100.

The boom 104 may be raised and lowered by a first hydraulic actuator 118. The stick 106 may be moved toward and outward with respect to the boom 104 by a second hydraulic actuator 122. A third hydraulic actuator 124 may be used to operate the hydraulic hammer 108 relative to the stick 106. Moreover, the chassis 110 may be rotated about a vertical-axis with respect to the drive system 112. The hydraulic hammer 108 further includes a work tool 130 configured to break rocks and penetrate through a work surface. In an embodiment, the machine 100 may be embodied as an excavator machine, where the hydraulic hammer 108 is mounted to replace an excavator bucket previously associated with the excavator. Consequently, the hydraulic hammer 108 may be operated by a hydraulic system of the excavator.

Figure 2:
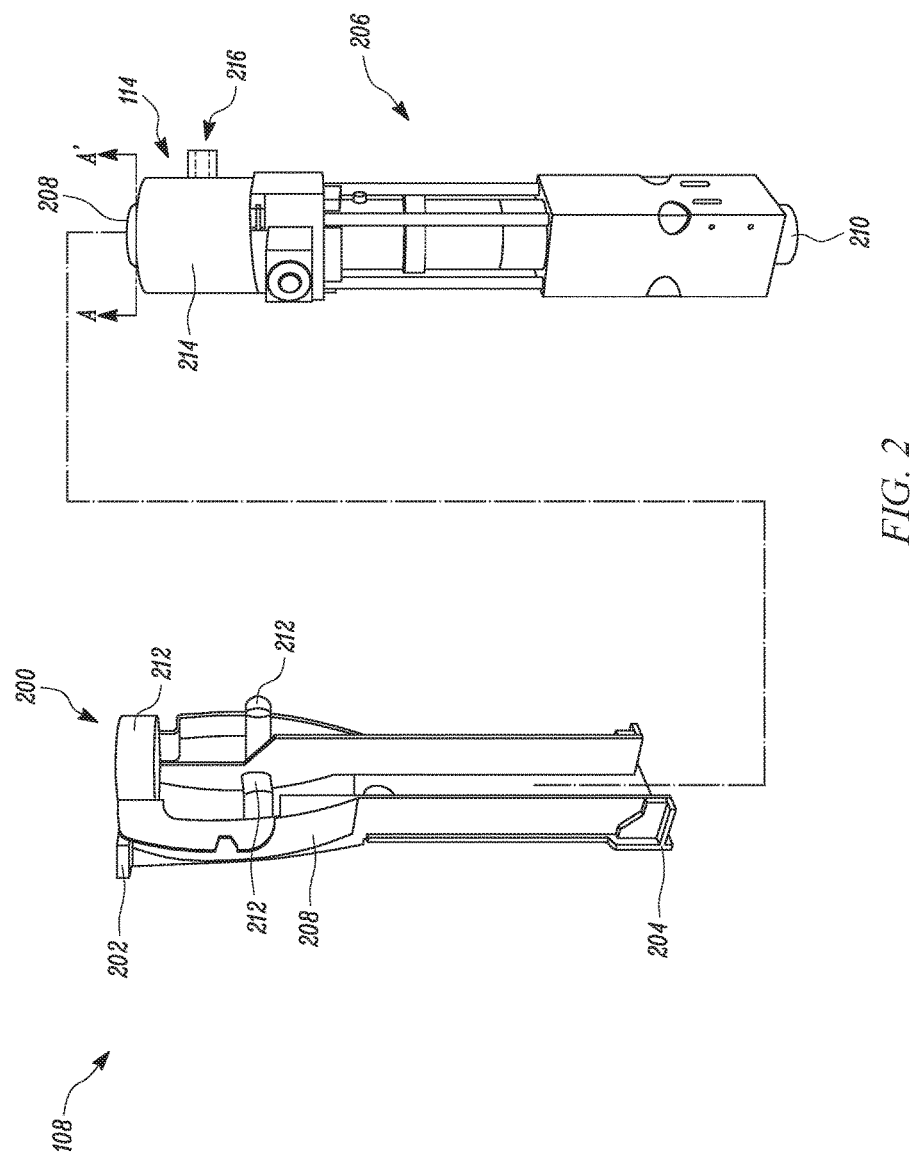
FIG. 2 is an exploded view of the hydraulic hammer, according to an embodiment of the present disclosure.

FIG. 2 illustrates an exploded view of the hydraulic hammer 108, according to an embodiment of the present disclosure. The hydraulic hammer 108 includes a housing member 200. A cut sectional view of the housing member 200 is shown in FIG. 2. The housing member 200 includes a first end 202 and a second end 204. The first end 202 may be configured to couple to the stick 106 of the implement system 102. The hydraulic hammer 108 further includes a power cell 206 having a first end 208 and a second end 210. The power cell 206 may be received through the second end 204 of the housing member 200. The second end 210 of the power cell 206 is coupled to the work tool 130. More particularly, one end of the work tool 130 is received into the power cell 206 adjacent to the second end 210 and another end of the work tool 130 is configured to engage with the work surface.

The power cell 206 is disposed within the housing member 200 with the help of a buffer system 212. The buffer system 212 may act as a vibration dampening mechanism between the power cell 206 and the housing member 200. In operation, the power cell 206 is subjected to impact loads due to contact of the work tool 130 with the work surface and hardness thereof. Such impact loads, if transferred to the hydraulic hammer 108, may cause wear of various components of the hydraulic hammer 108, particularly to the housing member 200 and the power cell 206.

The power cell 206 includes an accumulator 214 disposed adjacent to the first end 208 of the power cell 206. The accumulator 214 is configured to store gas, such as nitrogen, at a desired pressure for facilitating operation of the hydraulic hammer 108. The accumulator 214 includes a pressure indicator 216 configured to provide a visual indication of the desired pressure of the gas within the accumulator 214. More particularly, the pressure indicator 216 is configured to provide a visual indication of a pressure of the gas stored within the accumulator 214 at any time during an operating state of the hydraulic hammer 108 or a non-operating state of the hydraulic hammer 108.

Figure 3:
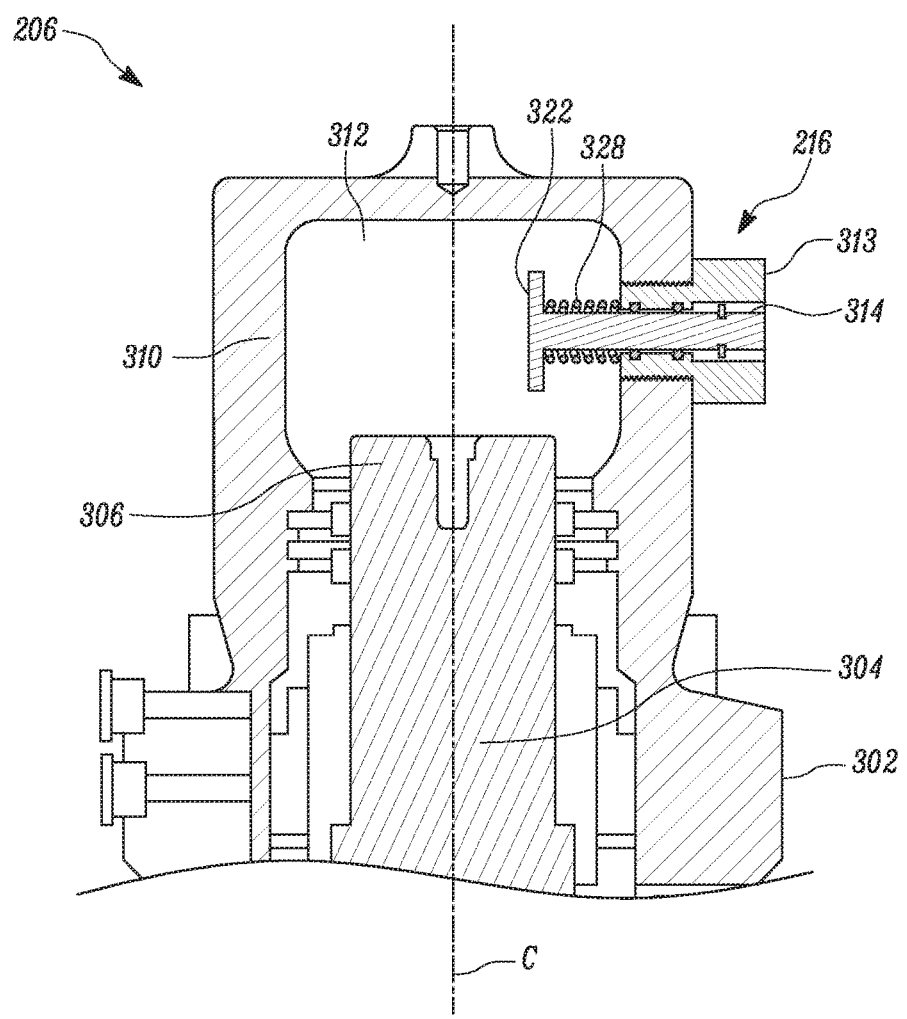
FIG. 3 is a sectional view of a portion of a power cell taken along line A-A' of FIG. 2 showing an accumulator and a pressure indicator disposed in the accumulator, according to an embodiment of the present disclosure.

FIG. 3 illustrates a sectional view of the power cell 206 of the hydraulic hammer 108, according to an embodiment of the present disclosure. The power cell 206 includes a case 302 configured to slidably dispose a piston 304 therein. The piston 304 has a first end 306 configured to communicate with the accumulator 214 and a second end (not shown) configured to contact with the work tool 130. The piston 304 is further actuated by the hydraulic system of the machine 100 for operation of the hydraulic hammer 108. The accumulator 214 includes a wall housing 310 coupled to the case 302 of the power cell 206. The wall housing 310 is configured to define a chamber 312 therein in association with the first end 306 of the piston 304. The chamber 312 may define a volume which may be varied based on an upward and a downward movement of the piston 304.

In an example, the accumulator 214 may be charged with the gas at the desired pressure before start of the operation of the hydraulic hammer 108. As such, the accumulator 214 is configured to store the compressed gas therein. The desired pressure of the gas may correspond to a predefined maximum pressure of the gas to be maintained within the chamber 312 of the accumulator 214 for desired performance of the hydraulic hammer 108. The desired pressure of the gas may be set during charging of the accumulator 214. The desired pressure of the gas may be determined based on various parameters including, but not limited to, change in pressure of the gas due to the upward and downward movement of the piston 304, and a type of the operation to be carried out in the work surface. After a prolonged period of operation of the hydraulic hammer 108, the pressure of the gas within the accumulator 214 may decrease to a minimum pressure. If the pressure of the gas goes below the minimum pressure, then the performance of the hydraulic hammer 108 may drop. Hence, the pressure of the gas is maintained at the desired pressure for the desired performance of the hydraulic hammer 108.

The pressure indicator 216 includes a sleeve member 313 and a plunger 314 slidably disposed within the sleeve member 313. The sleeve member 313 is configured to couple to an opening 316 defined in the wall housing 310 of the accumulator 214. The plunger 314 is configured to move between a first position 402 (shown in FIG. 5A) and a second position 404 (shown in FIG. 5B) with respect to the sleeve member 313. The opening 316 may be defined at any location in the wall housing 310, such that the plunger 314 may be disposed laterally with respect to a central axis 'C' of the power cell 206.

Figure 4:
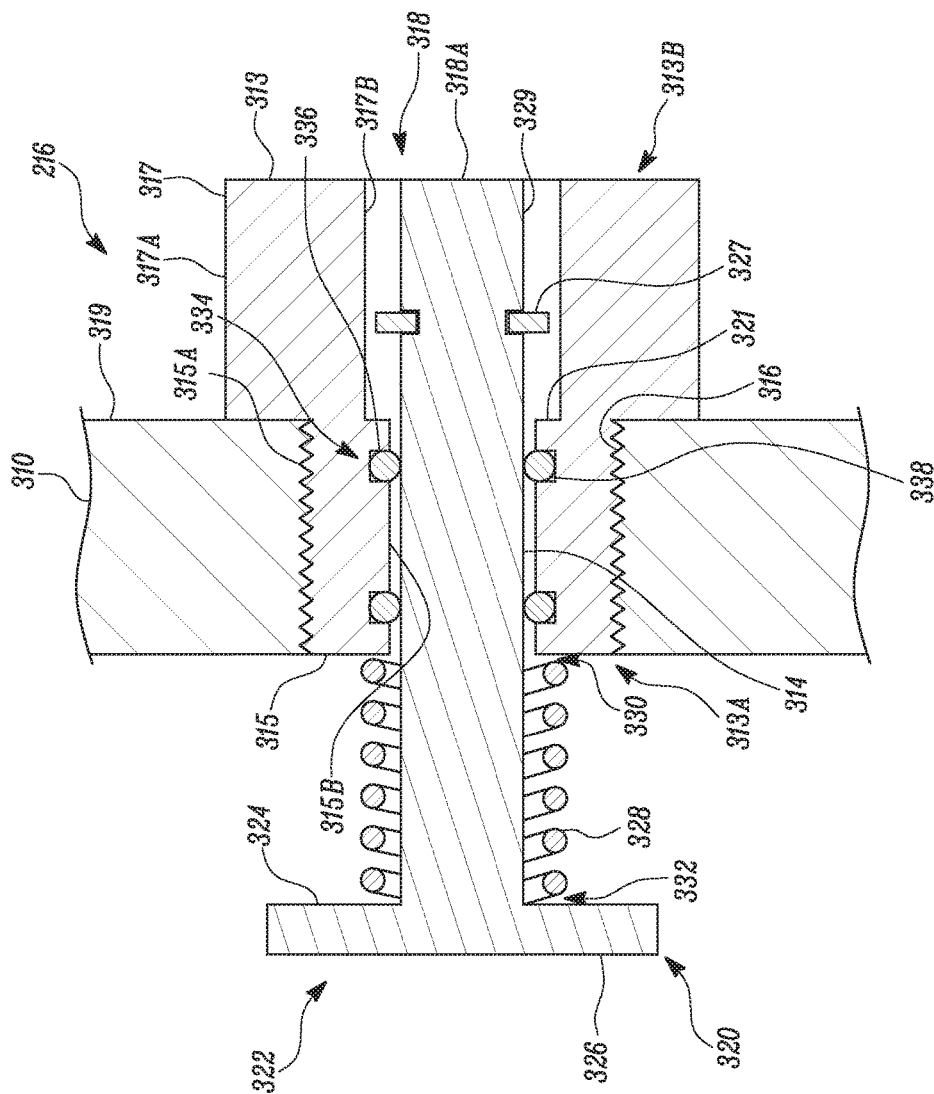
FIG. 4 is an enlarged view of the pressure indicator coupled to a wall housing of the accumulator, according to an embodiment of the present disclosure.

FIG. 4 illustrates an enlarged view of the pressure indicator 216 coupled to the wall housing 310 of the accumulator 214, according to an embodiment of the present disclosure. In the illustrated embodiment, the sleeve member 313 is a hollow cylindrical member having an inner end 313A and an outer end 313B. The sleeve member 313 further includes a first portion 315 adjacent to the inner end 313A and a second portion 317 adjacent to the outer end 313B. Further, the second portion 317 extends from the first portion 315, as shown in FIG. 4. The first portion 315 includes a first outer surface 315A and a first inner surface 315B. The first outer surface 315A includes threads to engage with threads formed on an inner surface (not shown) of the opening 316 of the wall housing 310. Thus, the sleeve member 313 is removably attached within the opening 316 of the wall housing 310 of the accumulator 214. The second portion 317 includes a second outer surface 317A and a second inner surface 317B. An outer diameter defined by the second outer surface 317A is greater than an outer diameter defined by the first outer surface 315A. As such, in assembled position of the sleeve member 313, the second portion 317 abuts an outer surface 319 of the wall housing 310. Similarly, an inner diameter defined by the second inner surface 317B is greater than an inner diameter defined by the first inner surface 315B. As such, a step portion 321 is defined between the first inner surface 315B and the second inner surface 317B.

The plunger 314 may be an elongated body having a first end 318 and a second end 320. The first end 318 defines an end face 318A. The first end 318 is disposed outside the wall housing 310 of the accumulator 214 and the second end 320 of the plunger 314 is disposed inside the wall housing 310. Specifically, the first end 318 of the plunger 314 is disposed within the second portion 317 of the sleeve member 313. In the illustrated embodiment, the plunger 314 has a circular cross section having an outer diameter less than the inner diameters of the first inner surface 315B and the second inner surface 317B. In other embodiments, cross section of the plunger 314 may be a square, a rectangle, an ellipse, a polygon, or any other shape known in the art.

In an alternative embodiment, the plunger 314 may include a plurality of pressure indication marks defined adjacent to the first end 318 of the plunger 314. Each of the plurality of pressure indication marks may be defined to provide a visual indication about the change in pressure of the gas within the accumulator 214. More particularly, a position of each of the plurality of pressure indication marks with reference to the sleeve member 313 may provide the visual indication of the pressure of the gas within the accumulator 214. In the case of plurality of pressure indication marks, the change in pressure of the gas may be precisely determined based on the position of each of the plurality of pressure indication marks with the sleeve member 313. In another embodiment, one pressure indication mark may be defined adjacent to the first end 318 of the plunger 314. The position of the pressure indication mark may provide the visual indication to the operator as to whether the pressure of the gas within the accumulator 214 is below or above the desired pressure.

In an example, the plurality of pressure indication marks may include at least one of a color mark and an indicator line to indicate the pressure of the gas within the accumulator 214. Each of the plurality of pressure indication marks may be provided with a different color to visually indicate the change in pressure of the gas. Similarly, each of the plurality of pressure indication marks may be provided with different indicator line type to visually indicate the change in pressure of the gas. The different indicator line type may be machined adjacent to the first end 318 of the plunger 314.

The plunger 314 further includes a flange 322 coupled to the second end 320, which is distal to the first end 318 of the plunger 314. In an example, the flange 322 may be a circular plate. In one embodiment, the flange 322 may be an individual component separately coupled to the second end 320 of the plunger 314. In such a case, the flange 322 may be threaded and/or bolted to the plunger 314, or may be coupled via any coupling method known in the art. In another embodiment, the flange 322 may be integrally formed with the second end 320 of the plunger 314. The flange 322 includes an inner face 324 and an outer face 326. The inner face 324 is coupled to the plunger 314 and the outer face 326 is configured to receive an input indicative of the pressure of the gas within the accumulator 214. The input may correspond to a force applied on the plunger 314 due to the pressure of the gas acted on the outer face 326 of the flange 322. The plunger 314 moves between the first position 402 and a second position 404, based on the input indicative of the pressure of the gas within the accumulator 214. More specifically, the force generated by the pressure of the gas acting on a surface area of the outer face 326 of the flange 322 may cause movement of the plunger 314 between the first position 402 and the second position 404.

The plunger 314 further includes a stopping member 327 disposed adjacent to the first end 318 thereof. In the illustrated embodiment, the stopping member 327 is a spacer coupled around an outer surface 329 of the plunger 314. The spacer may be coupled to the plunger 314 via various coupling methods including, but not limited to, press fitting, snap fitting, bolting and welding. In another embodiment, the spacer may be integrally formed with the plunger 314. In yet another embodiment, the stopping member 327 may be a projection extending from the outer surface 329 of the plunger 314. In one example, the projection may be a separate component coupled to the plunger 314. In another example, the projection may be integrally formed with the plunger 314. The stopping member 327 is configured to engage with the step portion 321 of the sleeve member 313 at the first position 402 of the plunger 314.

The plunger 314 moves to the first position 402 when the pressure of the gas within the accumulator 214 is the predefined maximum pressure, and the plunger 314 moves to the second position 404 when the pressure of the gas within the accumulator 214 is the predefined minimum pressure. Further, the plunger 314 defines a travel distance between the first position 402 and the second position 404 thereof. Specifically, the plurality of the pressure indication marks may be marked within a distance defined in the plunger 314 based on the travel distance of the plunger 314. In an example, the travel distance of the plunger 314 may be between 4 millimeter (mm) and 8 mm.

The pressure indicator 216 further includes an elastic member 328 inserted over the plunger 314 and disposed between the wall housing 310 and the flange 322. In the illustrated embodiment, the elastic member 328 is an open coil spring. In other embodiments, the elastic member 328 may be a closed coil spring, a leaf spring, a torsional spring, or any other elastic member known in the art. Further, the elastic member 328 includes a first end 330 and a second end 332. The first end 330 of the elastic member 328 is in contact with the inner end 313A of the sleeve member 313. The second end 332 of the elastic member 328 is in contact with the inner face 324 of the flange 322. An outer diameter of the elastic member 328 may be less than or equal to an outer diameter of the flange 322, such that the second end 332 of the elastic member 328 is coupled to the inner face 324 of the flange 322. An inner diameter of the elastic member 328 may be greater than the outer diameter of the plunger 314, such that the plunger 314 may be inserted through the elastic member 328. In an assembled condition of the elastic member 328, the plunger 314 moves relative to the wall housing 310 against a biasing force of the elastic member 328 based on the pressure of gas within the accumulator 214.

The pressure indicator 216 further includes a sealing assembly 334. The sealing assembly 334 is disposed on the first outer surface 315A of the first portion 315 of the sleeve member 313. A pair of such sealing assemblies 334 is disposed on the first outer surface 315A of the first portion 315 of the sleeve member 313. One of the pair of the sealing assemblies 334 is discussed herein below for illustration purpose of the present disclosure. The sealing assembly 334 includes an annular groove 336 defined within the first outer surface 315A first portion 315 of the sleeve member 313. The sealing assembly 334 further includes a sealing member 338 disposed within the annular groove 336. The sealing member 338 is configured to abut the outer surface 329 of the plunger 314. In an example, the sealing member 338 may be an oil ring known in the art. In another example, the sealing member 338 may be a circular gasket. The sealing member 338 may be designed to be placed in the annular groove 336. In various examples, the sealing member 338 may be any other sealing mechanism that may be configured to engage with the outer surface of the plunger 314. The sealing member 338 is configured to restrict the gas from leakage from the accumulator 214 during movement of the plunger 314 between the first position 402 and the second position 404. Thus, the sealing assembly 334 is configured to prevent leakage of the gas during operating or non-operating state of the hydraulic hammer 108. In an alternative embodiment, the sealing assembly 334 may be integrally formed with the plunger 314. It may also be contemplated that additional one or more such sealing assemblies 334 may be provided in the second inner surface 317B of the second portion 317 of the sleeve member 313.

At the desired pressure of the gas within the accumulator 214, the end face 318A of the first end 318 of the plunger 314 is in a same plane defined by a surface of the outer end 313B of the sleeve member 313, as shown in FIG. 4. A position of the first end 318 of the plunger 314 (shown in FIG. 4) at the desired pressure of the gas within the accumulator 214 may be hereinafter referred to as the normal position. At the normal position, the desired pressure of the gas may act on the outer face 326 of the flange 322, such that the plunger 314 moves outward against the biasing force of the elastic member 328. The sealing assembly 334, in contact with the plunger 314, restricts the gas from leakage during such movement of the plunger 314. The biasing force of the elastic member 328 may be understood as a force that causes the elastic member 328 to retract to an uncompressed state. The biasing force of the elastic member 328 may be further determined based on various parameters including, but not limited to, a spring constant value of the elastic member 328 and a desired travel distance of the plunger 314. In an example, the spring constant value of the elastic member 328 may be in a range between 3.77 N/mm and 15 N/mm. Further, it may be understood that the force applied on the flange 322 due to the desired pressure of the gas may be greater than the biasing force of the elastic member 328.

Figure 5:
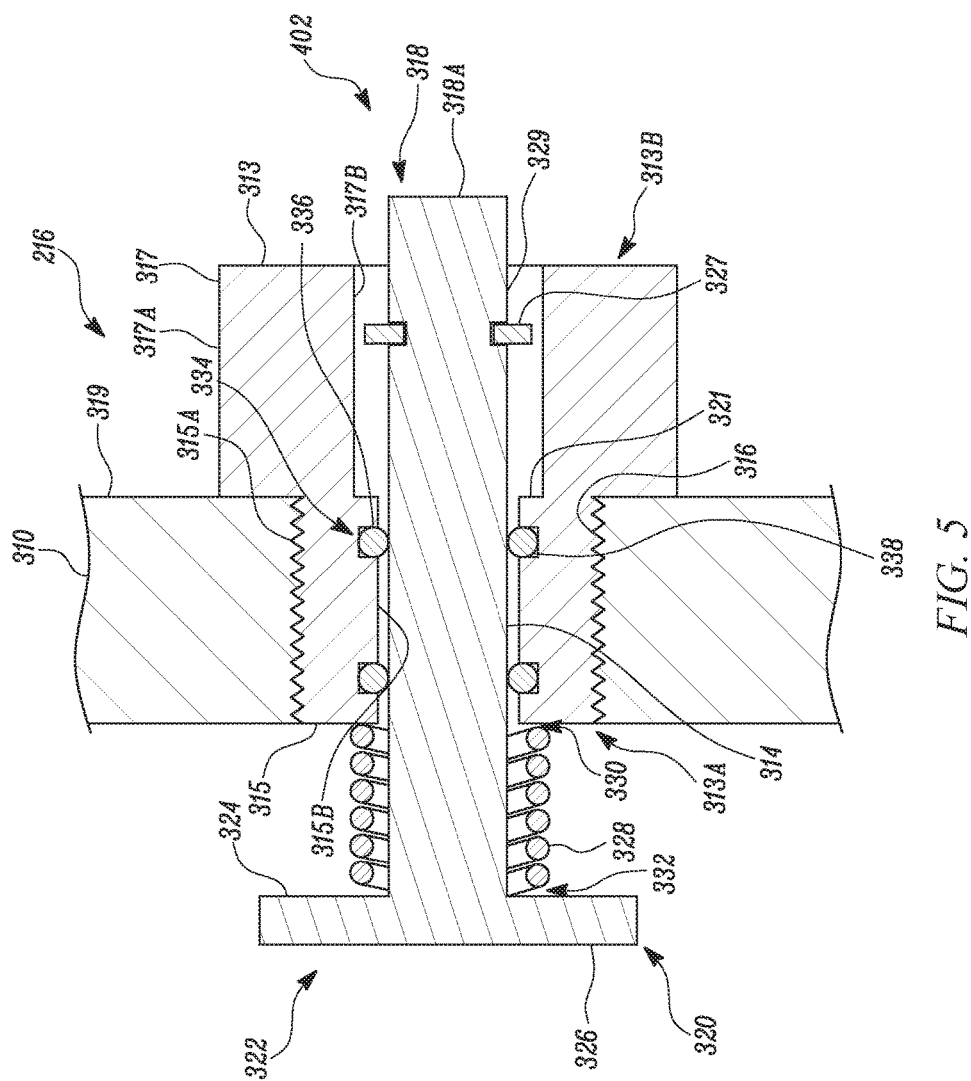
FIG. 5 is a sectional view of a first position of a plunger with respect to a sleeve member, according to an embodiment of the present disclosure.

FIG. 5 illustrates a sectional view of the first position 402 of the plunger 314 with respect to the sleeve member 313, according to an embodiment of the present disclosure. The first position 402 of the plunger 314 corresponds to a maximum pressure of the gas within the accumulator 214. In the first position 402, the maximum pressure of the gas may act on the outer face 326 of the flange 322, such that the plunger 314 moves outward against the biasing force of the elastic member 328. Further, the first end 318 of the plunger 314 moves beyond the normal position of the plunger 314 as the maximum pressure of the gas within the accumulator 214 is greater than the desired pressure of the gas to be maintained in the accumulator 214. It may be understood that the force applied on the flange 322 due to the maximum pressure may be greater than the biasing force of the elastic member 328. Further, it may be understood that the operator may tend to decrease the pressure of the gas within the accumulator 214 as the maximum pressure of the gas within the accumulator 214 may affect the performance of the hydraulic hammer 108.

Figure 6:
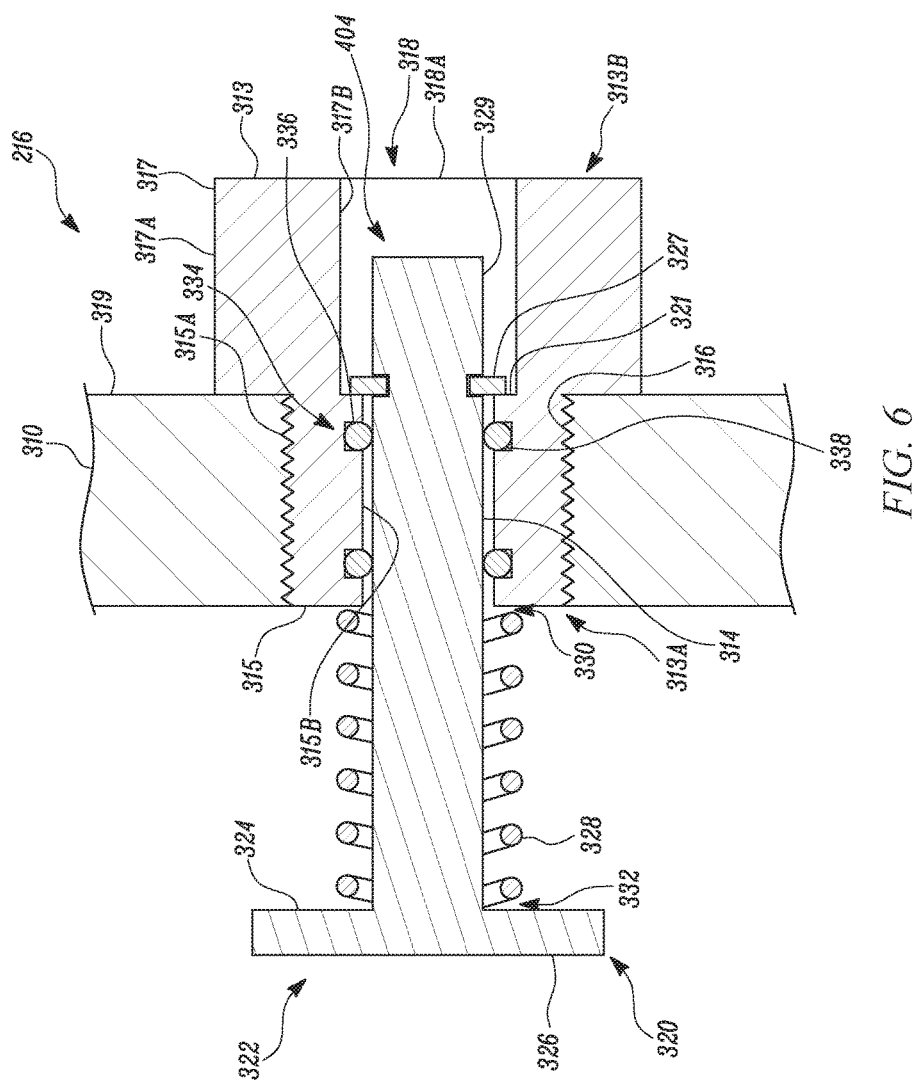
FIG. 6 is a sectional view showing a second position of the plunger with respect the sleeve member, according to an embodiment of the present disclosure.

FIG. 6 illustrates a sectional view showing a second position 404 of the plunger 314 with respect the sleeve member 313, according to an embodiment of the present disclosure. When the pressure of the gas decreases within the accumulator 214 after a prolonged operation of the hydraulic hammer 108, the plunger 314 moves to the second position 404. In the second position 404, the elastic member 328 may move to an uncompressed state thereof as the force applied on the flange 322, due to the pressure of the gas, is less than the biasing force of the elastic member 328. Further, the plunger 314 may move from the normal position to the second position 404 by the travel distance to indicate that the pressure of the gas within the accumulator 214 has reached to the minimum pressure. It may be understood that the operator may charge the accumulator 214 if the plunger 314 moves to the first position 402.

Figure 7:
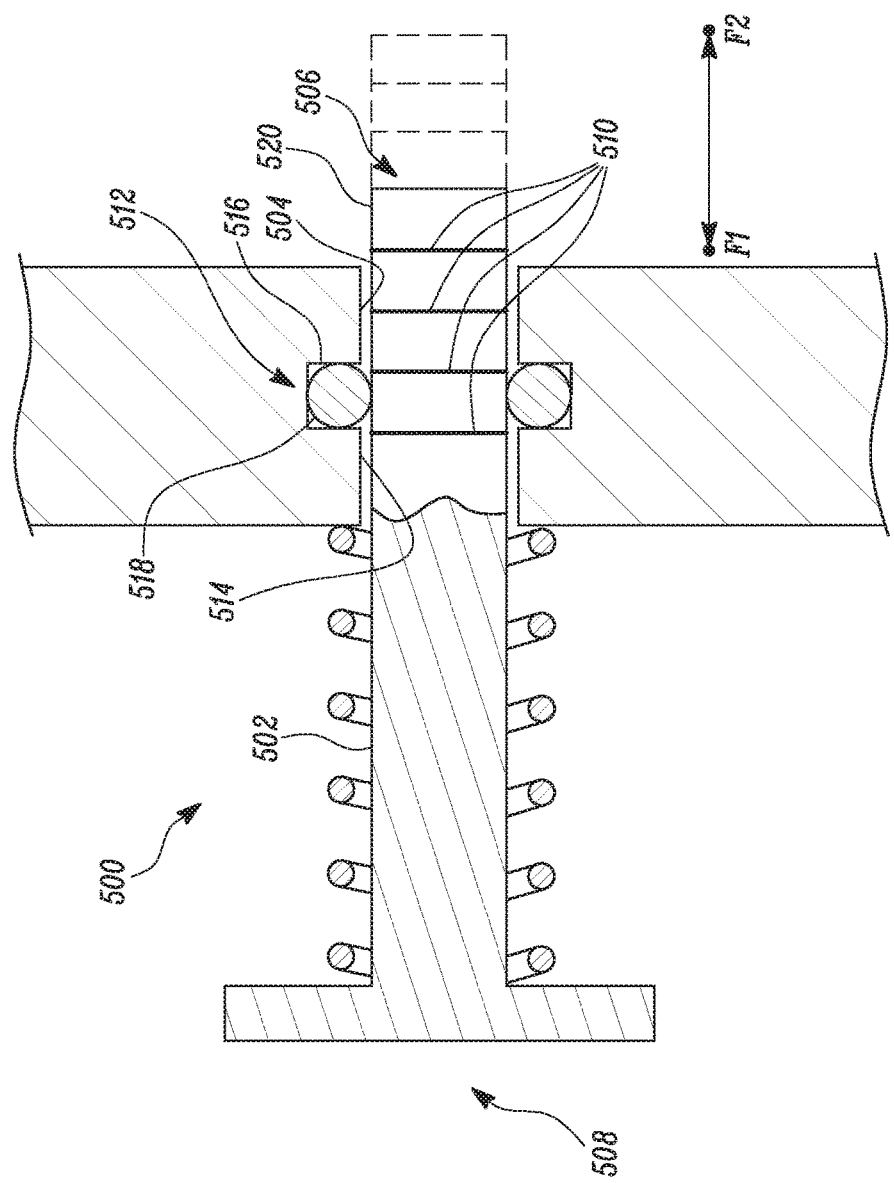
FIG. 7 illustrates a sectional view of a pressure indicator, according to another embodiment of the present disclosure.

FIG. 7 illustrates a sectional view of a pressure indicator 500, according to another embodiment of the present disclosure. The pressure indicator 500 includes a plunger 502 slidably disposed within an opening 504 defined in the wall housing 310 of the accumulator 214. The plunger 502 is configured to move between a first position 'F1' and a second position 'F2' with respect to the wall housing 310. The plunger 502 may be an elongated body having a first end 506 and a second end 508. The first end 506 is disposed outside the wall housing 310 of the accumulator 214 and the second end 508 is disposed inside the wall housing 310. A plurality of pressure indication marks 510 defined adjacent to the first end 506 of the plunger 502. Each of the plurality of pressure indication marks 510 is defined to provide a visual indication about change in pressure of the gas within the accumulator 214. More particularly, a position of each of the plurality of pressure indication marks 510 with reference to the outer surface 319 of the wall housing 310 provides the visual indication of the pressure of the gas within the accumulator 214. In an example, the plurality of pressure indication marks 510 may include at least one of a color mark and an indicator line to indicate the pressure of the gas within the accumulator 214. The plunger 502 further includes the flange 322 coupled to the second end 508 thereof. The pressure indicator 500 further includes the elastic member 328 inserted over the plunger 502 and disposed between the wall housing 310 and the flange 322. The pressure indicator 500 further includes a sealing assembly 512. The sealing assembly 512 is disposed on an inner surface 514 of the opening 504. The sealing assembly 512 includes an annular groove 516 defined within the inner surface 514 of the opening 504. The sealing assembly 512 further includes a sealing member 518 disposed within the annular groove 516. The sealing member 518 is configured to restrict the gas from leakage from the accumulator 214 during movement of the plunger 502 between the first position 'F1' and the second position 'F2'.

As shown in FIG. 7, the plunger 314 includes four pressure indication marks 510. Each of the four pressure indication marks 510 may be defined from the first end 506 of the plunger 502 at an equal distance or varying distance. If the four pressure indication marks 510 are visible outside the wall housing 310 of the accumulator 214, then the operator may understand that the pressure of the gas in the accumulator 214 is at the maximum pressure. If two pressure indication marks 510 are visible outside the wall housing 310 of the accumulator 214, then the operator may understand that the pressure of the gas in the accumulator 214 is below the maximum pressure but above the minimum pressure. If only one pressure indication mark 510 is visible outside the wall housing 310 of the accumulator 214, then the operator may understand that the pressure of the gas in the accumulator 214 is at the minimum pressure. In such a case, the operator may charge the accumulator 214 to increase the pressure of the gas within the accumulator 214 to the desired pressure. In another example, the pressure indicator 216 may include two pressure indication marks 510, one of which may represent the maximum pressure and another of which may represent the minimum pressure.

INDUSTRIAL APPLICABILITY

The present disclosure relates to the pressure indicator 216 for the hydraulic hammer 108. The pressure indicator 216 includes the sleeve member 313 and the plunger 314 slidably disposed within the sleeve member 313. The plunger 314 is movable between the first position 402 and the second position 404 with respect to the sleeve member 313, such that the position of the end face 318A of the first end 318 of the plunger 314 with respect to the outer end 313B of the sleeve member 313 is visible to the operator from outside the power cell 206. The pressure of the gas within the accumulator 214 pushes the plunger 314 against the biasing force of the elastic member 328 and moves the plunger 314 between the first position 402 and the second position 404 to indicate the pressure of the gas within the accumulator 214. In addition, the accumulator 214 may provide a cushioning effect to the hydraulic hammer 108, by reducing shocks caused due to rapid operation of the hydraulic hammer 108.

Figure 8:
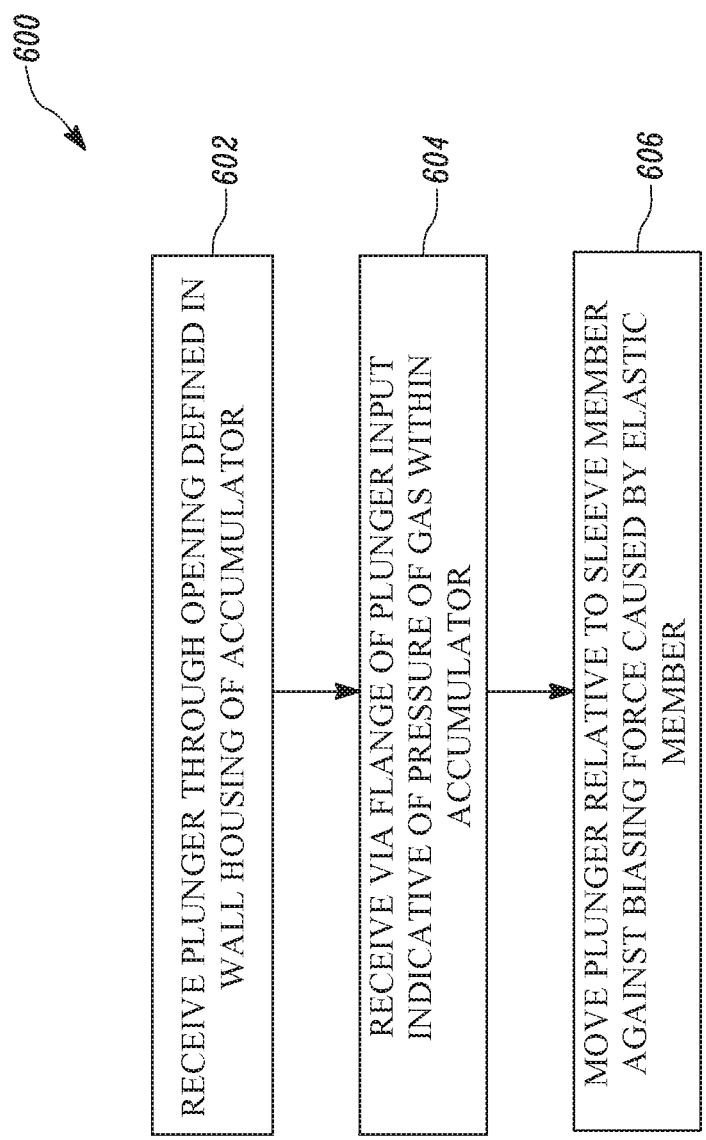
FIG. 8 is a flowchart of a method for visual indication of a pressure of gas within the accumulator, according to an embodiment of the present disclosure.

FIG. 8 illustrates a flowchart of the method 600 for visual indication of the pressure of the gas within the accumulator 214, according to an embodiment of the present disclosure. At step 602, the method 600 includes receiving the plunger 314 within the opening 316 defined in the wall housing 310 of the accumulator 214. As described earlier, the plunger 314 includes the first end 318 disposed outside the wall housing 310 of the accumulator 214 and the second end 320 having the flange 322 disposed inside the wall housing 310 of the accumulator 214. Further, the plunger 314 is movable between the first position 402 and the second position 404 with respect to the sleeve member 313 coupled to the opening 316. At step 604, the method 600 includes receiving, via the flange 322 of the plunger 314, the input indicative of the pressure of the gas within the accumulator 214.

At step 606, the method 600 includes moving the plunger 314 relative to the sleeve member 313 against the biasing force caused by the elastic member 328. The position of the position of the first end 318 of the plunger 314 with reference to the sleeve member 313 provides the visual indication of the pressure of the gas within the accumulator 214. Further, the plunger 314 is movable between the first position 402 and the second position 404 relative to the sleeve member 313 against the biasing force of the elastic member 328. The plunger 314 moves to the first position 402 when the pressure of the gas within the accumulator 214 is in the predefined maximum pressure and the plunger 314 moves to the second position 404 when the pressure of the gas within the accumulator 214 is in the predefined minimum pressure.

Further, based on the position of the plunger 314, volume available within the accumulator 214 may be determined by the operator. Accordingly, the charging of the accumulator 214 may be performed as and when required, which was otherwise performed without the knowledge of volume available within the accumulator 214. As such, charging the accumulator 214 by knowing actual pressure of the gas within the accumulator 214 may lead to lesser operation cost.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A pressure indicator for a hydraulic hammer, the pressure indicator comprising:
   a sleeve member configured to couple to an opening defined in a wall housing of an accumulator of the hydraulic hammer;
   a plunger slidably disposed within the sleeve member and movable between a first position and a second position with respect to the sleeve member, the plunger comprising:
      a first end disposed outside the wall housing of the accumulator; and
      a flange coupled to a second end, wherein the second end is distal to the first end, and disposed inside the wall housing of the accumulator; and
   an elastic member inserted over the plunger and disposed between the wall housing of the accumulator and the flange,
   wherein the plunger is moveable between the first position and the second position relative to the sleeve member against a biasing force of the elastic member based on a pressure of gas within the accumulator, and wherein a position of the first end of the plunger with reference to an outer end of the sleeve member provides a visual indication of the pressure of the gas within the accumulator, and
   wherein the plunger comprises a stopping member disposed adjacent to the first end thereof, the stopping member configured to engage with a step portion defined at an inner surface of the sleeve member at the first position of the plunger.

2. The pressure indicator of claim 1, wherein the sleeve member comprises a first portion and a second portion extending from the first portion, and wherein the first portion is removably attached within the opening of the wall housing of the accumulator.

3. The pressure indicator of claim 2 comprising a sealing assembly disposed between the sleeve member and the plunger, the sealing assembly configured to restrict the gas from leakage during movement of the plunger between the first position and the second position.

4. The pressure indicator of claim 3, wherein the sealing assembly comprises:
- an annular groove defined within an inner surface of the sleeve member disposed within the opening of the wall housing of the accumulator; and
- a sealing member disposed within the annular groove, the sealing member configured to abut an outer surface of the plunger.

5. The pressure indicator of claim 1, wherein the elastic member comprises a first end in contact with the wall housing of the accumulator and a second end in contact with the flange.

6. The pressure indicator of claim 1, wherein the flange comprises an outer face configured to receive an input indicative of the pressure of the gas within the accumulator.

7. The pressure indicator of claim 1, wherein the elastic member is an open coil spring.

8. The pressure indicator of claim 1, wherein a travel distance defined by the plunger between the first position and the second position is in a range between 4 mm and 8 mm.

9. A hydraulic hammer, comprising:
- a housing member; and
- a power cell disposed within the housing member, the power cell comprising an accumulator for storing a gas, the accumulator comprising a pressure indicator configured to provide a visual indication of a pressure of the gas within the accumulator, the pressure indicator comprising:
  - a sleeve member configured to couple to an opening defined in a wall housing of the accumulator;
  - a plunger slidably disposed within the sleeve member and movable between a first position and a second position with respect to the sleeve member, the plunger comprising:
    - a first end disposed outside the wall housing of the accumulator; and
    - a flange coupled to a second end, wherein the second end is distal to the first end, and disposed inside the wall housing of the accumulator; and
  - an elastic member inserted over the plunger and disposed between the wall housing and the flange,
  - wherein the plunger is moveable between the first position and the second position relative to the sleeve member against a biasing force of the elastic member based on the pressure of the gas within the accumulator, and wherein a position of the first end of the plunger with reference to an outer end of the sleeve member provides a visual indication indicative of the pressure of the gas within the accumulator, and
  - wherein the plunger comprises a stopping member disposed adjacent to the first end thereof, the stopping member configured to engage with a step portion defined at an inner surface of the sleeve member at the first position of the plunger.

10. The hydraulic hammer of claim 9, wherein the sleeve member comprises a first portion and a second portion extending from the first portion, and wherein the first portion is removably attached within the opening of the wall housing of the accumulator.

11. The hydraulic hammer of claim 10, wherein the pressure indicator comprises a sealing assembly disposed between the sleeve member and the plunger, the sealing assembly configured to restrict the gas from leakage during movement of the plunger between the first position and the second position.

12. The hydraulic hammer of claim 11, wherein the sealing assembly comprises:
- an annular groove defined within an inner surface of the sleeve member disposed within the opening of the wall housing of the accumulator; and
- a sealing member disposed within the annular groove, the sealing member configured to abut an outer surface of the plunger.

13. The hydraulic hammer of claim 9, wherein the elastic member comprises a first end in contact with the wall housing of the accumulator and a second end in contact with the flange.

14. The hydraulic hammer of claim 9, wherein the flange comprises a receiving surface configured to receive an input indicative of the pressure of the gas within the accumulator.

15. The hydraulic hammer of claim 9, wherein the elastic member is an open coil spring.

16. The hydraulic hammer of claim 9, wherein a travel distance defined by the plunger between the first position and the second position is in a range between 4 mm and 8 mm.

* * * * *